US011090299B2

(12) United States Patent
Park et al.

(10) Patent No.: US 11,090,299 B2
(45) Date of Patent: Aug. 17, 2021

(54) ORAL SOLID FORMULATION CONTAINING IRINOTECAN AND METHOD OF PREPARING THE SAME

(71) Applicant: HANMI PHARM. CO., LTD., Hwaseong-si (KR)

(72) Inventors: Caleb Hyung Min Park, Goyang-si (KR); Myeong Ki Jung, Suwon-si (KR); Jin Cheul Kim, Seoul (KR); Yong Il Kim, Suwon-si (KR); Jae Hyun Park, Suwon-si (KR); Jong Soo Woo, Suwon-si (KR)

(73) Assignee: HANMI PHARM. CO., LTD., Hwaseong-si (KR)

( * ) Notice: Subject to any disclaimer, the term of this patent is extended or adjusted under 35 U.S.C. 154(b) by 0 days.

(21) Appl. No.: 15/735,313

(22) PCT Filed: Jun. 20, 2016

(86) PCT No.: PCT/KR2016/006513
§ 371 (c)(1),
(2) Date: Dec. 11, 2017

(87) PCT Pub. No.: WO2017/003120
PCT Pub. Date: Jan. 5, 2017

(65) Prior Publication Data
US 2018/0153878 A1 Jun. 7, 2018

(30) Foreign Application Priority Data
Jun. 30, 2015 (KR) ........................ 10-2015-0093413

(51) Int. Cl.
*A61K 31/4745* (2006.01)
*A61P 35/00* (2006.01)
*A61K 47/12* (2006.01)
*A61K 47/20* (2006.01)
*A61K 9/20* (2006.01)
*A61K 9/16* (2006.01)
*A61K 9/48* (2006.01)

(52) U.S. Cl.
CPC ........ *A61K 31/4745* (2013.01); *A61K 9/1617* (2013.01); *A61K 9/1682* (2013.01); *A61K 9/2013* (2013.01); *A61K 9/2018* (2013.01); *A61K 9/2027* (2013.01); *A61K 9/2054* (2013.01); *A61K 47/12* (2013.01); *A61K 47/20* (2013.01); *A61P 35/00* (2018.01); *A61K 9/4858* (2013.01); *A61K 2300/00* (2013.01)

(58) Field of Classification Search
CPC ............. A61K 31/4745; A61K 9/1617; A61K 9/1682; A61K 9/2013; A61K 9/2018; A61K 9/2027; A61K 9/2054; A61K 47/12; A61K 47/20; A61P 35/00
See application file for complete search history.

(56) References Cited

U.S. PATENT DOCUMENTS

| | | | |
|---|---|---|---|
| 4,604,463 A | 8/1986 | Miyasaka et al. | |
| 6,881,420 B2 | 4/2005 | Flashner-Barak et al. | |
| 8,852,632 B2 | 10/2014 | Pourkavoos et al. | |
| 2002/0147208 A1* | 10/2002 | Fleshner-Barak | A61K 9/0065 514/283 |
| 2003/0109514 A1 | 6/2003 | Lauria et al. | |
| 2005/0208146 A1 | 9/2005 | Miller | |
| 2006/0030578 A1 | 2/2006 | Ahmad et al. | |
| 2007/0299099 A1* | 12/2007 | Shimizu ............... | C07D 491/22 514/283 |

FOREIGN PATENT DOCUMENTS

| | | | |
|---|---|---|---|
| CN | 1325305 A | 12/2001 | |
| CN | 101283983 A | 10/2008 | |
| CN | 102617584 A | 8/2012 | |
| EP | 2 238 557 A1 | 6/2011 | |
| JP | 2002-154963 A | 5/2002 | |
| JP | 2004277374 A | 10/2004 | |
| RU | 2 382 648 C2 | 2/2010 | |
| WO | 99/65493 A1 | 12/1999 | |
| WO | 01/30351 A1 | 5/2001 | |
| WO | 03/074527 A1 | 9/2003 | |
| WO | 2006127926 A2 | 11/2006 | |
| WO | 2010/015688 | 2/2010 | |
| WO | 2014/085371 A1 | 6/2014 | |
| WO | 2015/107131 | 7/2015 | |
| WO | WO-2015107131 A1 * | 7/2015 | ........... C07D 491/22 |

OTHER PUBLICATIONS

Li et al., "Stability of irinotecan hydrochloride in aqueous solutions," Am J Health-Syst Pharm, vol. 59, Mar. 15, 2002.*
Yassin et al., "The Disintegration Process in Microcrystalline Cellulose Based Tables, Part 1: Influence of Temperature, Porosity and Superdisintegrants," published Jun. 12, 2015.*
International Search Report for PCT/KR2016/006513 dated Nov. 10, 2016 [PCT/ISA/210].
Written Opinion for PCT/KR2016/006513 dated Nov. 10, 2016 [PCT/ISA/237].
European Patent Office, Communication dated Sep. 11, 2018 by the European Patent Office in corresponding European Application No. 16 81 8153.
Machida et al., "Efficacy of nanoparticles containing irinotecan prepared using poly(DL-lactic acid) and poly(ethylene glycol)-poly(propylene giycol)-poly(ethylene glycol) against M5076 tumor in the early liver metastatic stage", S.T.P. Pharma Sciences, 13 (4), 2003, pp. 225-230.
The Industrial Property of Ecuadorian Institute of Intellectual Property: Communication dated Nov. 28, 2018 in Ecuadorian Application No. 2017-85443.
Naveen K. Thakral et al., "Soluplus-Solubilized Citrated Camptothecin—A Potential Drug Delivery Strategy in Colon Cancer" AAPS PharmSciTech, Mar. 2012, vol. 13, No. 1, pp. 59-66 (8 pages total).

(Continued)

Primary Examiner — Jared Barsky
(74) Attorney, Agent, or Firm — Sughrue Mion, PLLC

(57) ABSTRACT

An oral solid formulation includes irinotecan or a pharmaceutically acceptable salt thereof as an active ingredient, and an acidifying agent.

8 Claims, 2 Drawing Sheets

(56) References Cited

OTHER PUBLICATIONS

Galenic Notes Pharmaceutical operations with tablets (mixing, granulation, compression) Ignacio Navascués, Roche Laboratories, Basel (Switzerland) vol. 3, No. 8. Jun. 2002 (8 pages).
Dominican National Office of Industrial Property, Communication dated Nov. 14, 2019, issued in application No. P2017-0307.
Intellectual Property of India, Communication dated Jan. 23, 2020, issued in application No. 201717041628.
Bastin et al., "Salt Selection and Optimisation Procedures for Pharmaceutical New Chemical Entities", Organic Process Research & Development, 2000, vol. 4, 427-435.

* cited by examiner

【Figure 1】
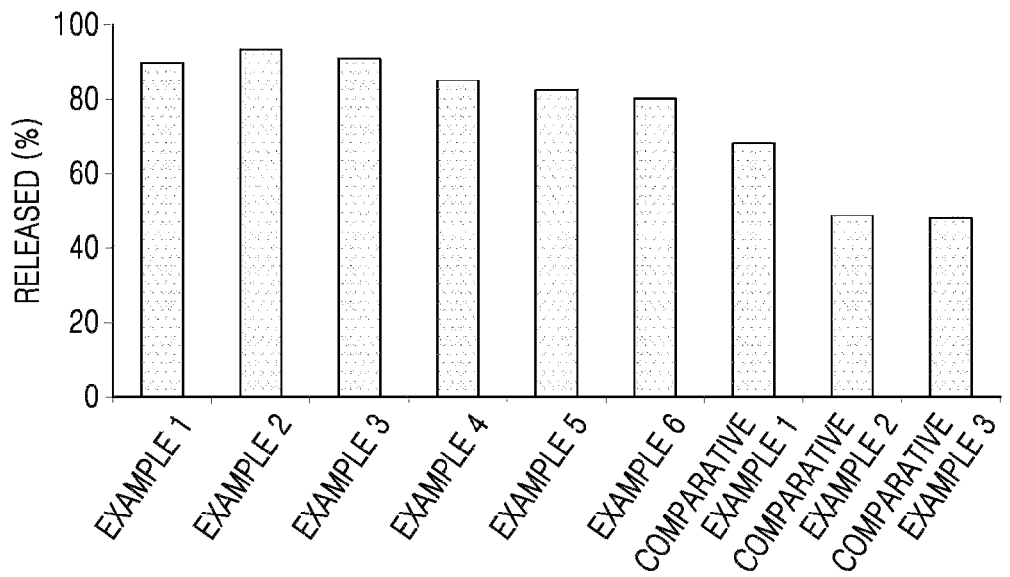
【Figure 2】
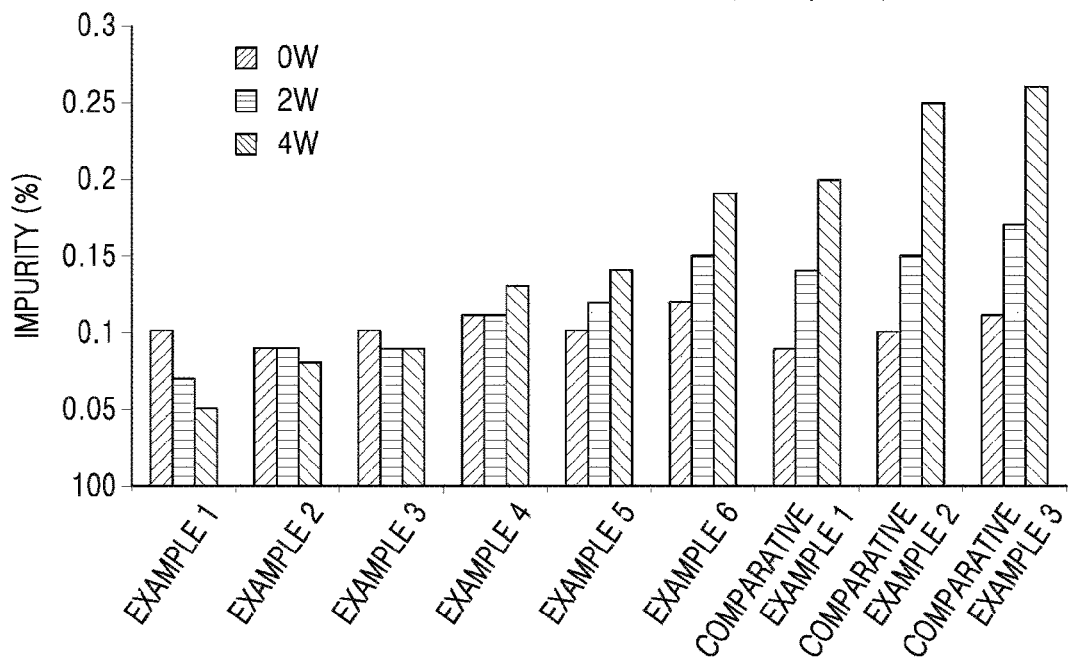

[Figure 3]
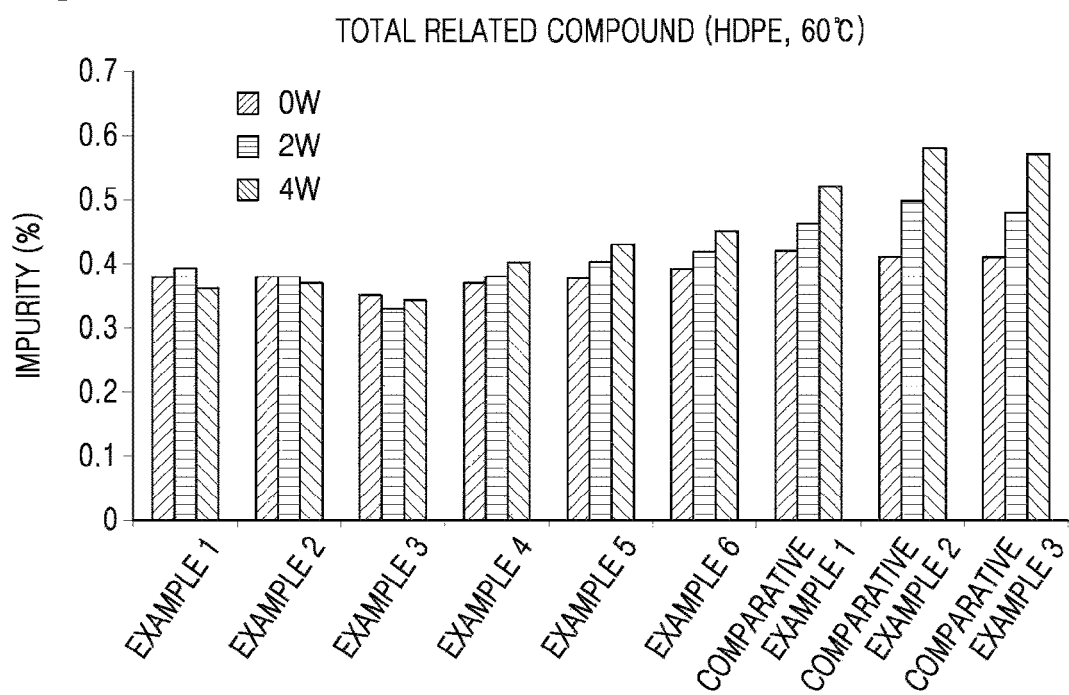

ORAL SOLID FORMULATION CONTAINING IRINOTECAN AND METHOD OF PREPARING THE SAME

CROSS REFERENCE TO RELATED APPLICATIONS

This application is a National Stage of International Application No. PCT/KR2016/006513 filed Jun. 20, 2016, claiming priority based on Korean Patent Application No. 10-2015-0093413 filed Jun. 30, 2015, the contents of all of which are incorporated herein by reference in their entirety.

TECHNICAL FIELD

The present disclosure relates to an oral solid formulation containing irinotecan and a method of preparing the same, and more particularly, to an oral solid formulation containing irinotecan with improved bioavailability and stability, and a method of preparing the same.

BACKGROUND ART

Irinotecan, a semisynthetic analog of camptothecin, is used as a cancer chemotherapeutic agent mainly against metastatic colorectal cancers. Irinotecan with the chemical name of (S)-4,11-diethyl-3,4,12,14-tetrahydro-4-hydroxy-3,14-dioxo-1H-pyrano[3',4':6,7]-indolizin o[1,2-b]quinolin-9-yl[1,4'-bipiperidine]-1'-carboxylate has a structure represented by Formula 1.

[Formula 1]

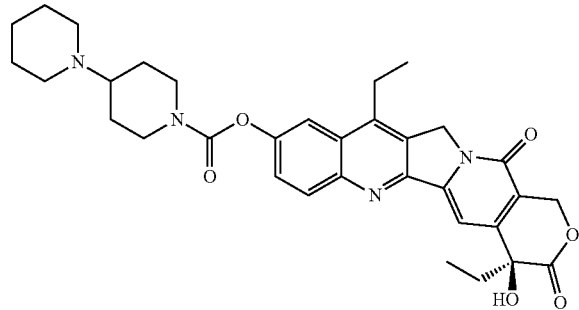

Irinotecan has been extensively researched through both preclinical and clinical test. Irinotecan was approved by the U.S. Food and Drug Administration (FDA) as therapy for colon cancer. Irinotecan induces antitumor activity in a wide range of various experimental tumor models, and has been researched on efficacy, specifically in lung cancer, stomach cancer, pancreatic cancer, non-Hodgkin's lymphoma, uterine cervix cancer, head and neck cancer, brain tumor, and ovarian cancer (WO 2001/030351).

Irinotecan is a prodrug which is metabolized in the liver, intestines, and tumors into an active metabolite SN-38 (7-ethyl-10-hydroxycamptothecin) by carboxylesterases. SN-38 has an efficacy as strong as about 100 to 1000 times of irinotecan.

Irinotecan has adverse effects such as severe diarrhea and extreme suppression of the immune system. Diarrhea caused by irinotecan may often lead to severe dehydration requiring hospitalization or intensive care. Irinotecan-associated immunesuppression may dramatically reduce white blood cell counts in the blood, in particular, the neurophils counts.

Efficacy of irinotecan is dependent on dosage regimen. Long-term lower dose is known to be more effective and less toxic, compared to short-term higher dose for irinotecan. Effective long-term exposure to irinotecan is oral administration, with a higher metabolic rate of total irinotecan to total SN-38 in oral administration than in intravenous (IV) administration. Therefore, there is a need for the development of oral irinotecan formulations, and in particular, oral irinotecan formulations that may secure sufficient bioavailability of irinotecan having poor solubility (EP 2328557 A) and that also may maintain the stability of the active ingredient with time.

DISCLOSURE

Technical Problem

The present disclosure provides an oral solid formulation containing irinotecan with improved bioavailability and stability of the active ingredient.

The present disclosure provides a method of preparing the oral solid formulation containing irinotecan with improved bioavailability and stability of the active ingredient.

Technical Solution

According to an aspect of the present invention, there is provided an oral solid formulation including: irinotecan or a pharmaceutically acceptable salt thereof; and an acidifying agent.

According to another aspect of the present invention, there is provided a method of preparing the oral solid formulation, the method including: forming granules comprising irinotecan or a pharmaceutically acceptable salt thereof, a diluent, and a binder; mixing the granules with a disintegrant and a lubricant to obtain a mixture; and optionally, formulating the resultant mixture, wherein, in the step of forming granules and/or mixing the granules, an acidifying agent is added.

Advantageous Effects

According to the one or more embodiments of the present disclosure, an irinotecan-containing oral solid formulation prepared using an acidifying agent may have a remarkably increased dissolution rate of the active ingredient, due to including the acidifying agent, and may ensure improved bioavailability when orally administered. The active ingredient of the irinotecan-containing oral solid formulation may also have high stability with time, and thus the irinotecan-containing oral solid formulation may ensure efficacy of irinotecan through oral administration, remarkably lowering the risk of side effects compared to conventional injection of irinotecan. Therefore, an irinotecan-containing oral solid formulation according to any of the embodiments may have improved efficacy and stability and reduced side effects.

DESCRIPTION OF DRAWINGS

FIG. 1 is a graph of dissolution rate in oral solid formulations of Examples 1 to 6 and Comparative Examples 1 to 3, illustrating the results of an 30-minute dissolution test performed according to the paddle method of the U.S. Pharmacopeia (USP) with 900 mL of purified water;

FIG. 2 is a graph illustrating the results of analyzing the amounts of unknown related compounds in the oral solid formulations of Examples 1 to 6 and Comparative Examples 1 to 3, after storage of each oral solid formulation in a high-density polyethylene (HDPE) bottle in a 60° C. chamber for 2 weeks or 4 weeks; and FIG. 3 is a graph illustrating the results of analyzing the amounts of a total related compound in the oral solid formulations of Examples 1 to 6 and Comparative Examples 1 to 3, after storage of each oral solid formulation in a HDPE bottle in a 60° C. chamber for 2 weeks or 4 weeks.

MODE FOR INVENTION

The present disclosure will be described with reference to exemplary embodiments.

Unless otherwise defined, all terms (including technical and scientific terms) used herein have the same meaning as commonly understood by one of ordinary skill in the art to which this invention belongs. Although exemplary methods or materials are listed herein, other similar or equivalent ones are also within the scope of the present invention. All publications disclosed as references herein are incorporated in their entirety by reference.

According to an aspect of the present disclosure, an oral solid formulation includes irinotecan or a pharmaceutically acceptable salt thereof as an active ingredient, and an acidifying agent.

The pharmaceutically acceptable salt may include an acid addition salt. The acid addition salt may include an inorganic acid salt or an organic acid salt.

The inorganic acid salt may include hydrochloride, phosphate, sulfate, or disulfate. However, embodiments are not limited thereto. The organic acid salt may include malate, maleate, citrate, fumarate, besylate, camsylate, or edisylate. However, embodiments are not limited thereto.

For example, the pharmaceutically acceptable salt of irinotecan may be hydrochloride, and in some embodiments, irinotecan hydrochloride hydrate, for example, irinotecan hydrochloride trihydrate.

As used herein, the term "acidifying agent" may mean any material that may lower a pH of a solution by being dissolved in water. In some embodiments, the acidifying agent may be an inorganic acid and/or organic acid that may lower a pH of a solution to 5 or less by being dissolved in water.

The inorganic acid may include hydrochloric acid, phosphoric acid, potassium dihydrogen phosphate, sodium dihydrogen phosphate, or any combinations thereof. However, embodiments are not limited thereto. The organic acid may include citric acid, lactic acid, tartaric acid, fumaric acid, phthalic acid, acetic acid, oxalic acid, malonic acid, adipic acid, phytic acid, succinic acid, glutaric acid, maleic acid, malic acid, mandelic acid, ascorbic acid, benzoic acid, methanesulfonic acid, capric acid, caproic acid, caprylic acid, lauric acid, arachidic acid, erucic acid, linoleic acid, linolenic acid, oleic acid, palmitic acid, myristic acid, edisilic acid, stearic acid, or any combinations thereof. However, embodiments are not limited thereto.

In some embodiments, the acidifying agent may be a C2-C20 organic acid including a carboxyl group (COOH) or a sulfonic acid group ($SO_3H$).

In some embodiments, the acidifying agent may be selected from the group consisting of acetic acid, adipic acid, citric acid, ascorbic acid, erythorbic acid, lactic acid, propionic acid, tartaric acid, fumaric acid, formic acid, oxalic acid, camsylate, malic acid, maleic acid, edisilic acid, palmitic acid, stearic acid, and any combinations thereof.

In some embodiments, the acidifying agent may be selected from the group consisting of acetic acid, citric acid, lactic acid, and any combinations thereof.

In some embodiments, although depending on a type of the acidifying agent, the amount of the acidifying agent in the oral solid formulation may be a level at which a dissolution medium from a dissolution test for about 30 minutes according to the paddle method of the U.S. Pharmacopeia (USP) with 900 mL of purified water may have a pH of about 1 to about 5. For example, the amount of the acidifying agent in the oral solid formulation may be from about 0.2 to about 10.0 parts by weight, and in some embodiments, about 0.2 to about 5 parts by weight, based on 1 part by weight of the irinotecan or a pharmaceutically acceptable salt thereof.

In some embodiments, the oral solid formulation may be an oral solid formulation that may obtain a dissolution medium of a pH of about 1 to about 5 in a dissolution test for about 30 minutes according to the paddle method of the USP with 900 mL of purified water.

Due to including the acidifying agent, the irinotecan, which is known as a drug with poor solubility, of the oral solid formulation may have a remarkably increased dissolution rate, and thus, the oral solid formulation may have a remarkably increased bioavailability when orally administered. This increased bioavailability enables the solid formulation to be orally administered, and consequentially improve a patient's compliance.

In some embodiments, the dissolution rate of the active ingredient of the oral solid formulation may be about 80% or greater in 45 minutes of a dissolution test according to the paddle method of the USP with 900 mL of purified water, and in some other embodiments, the dissolution rate of the active ingredient is about 80% or greater in 30 minutes of the dissolution test. According to a test result, the dissolution rate of the active ingredient of the oral solid formulation including irinotecan and the acidifying agent was found be markedly increased, compared to when no acidifying agent is included or a basifying agent is included (Test Example 2).

The stability of the irinotecan of the oral solid formulation according to any of the above-described embodiments may be remarkably increased with time, due to including the acidifying agent. According to a test result, the oral solid formulation including irinotecan and the acidifying agent was found to have a remarkable reduction in yield increase rate of related compounds with time, compared to when no acidifying agent is included or a basifying agent is included (Test Example 3).

As used herein, the term "solid formulation" may mean a formulation prepared by molding or encapsulating drugs into a predetermined shape. The oral solid formulation may be formulated as, but is not limited to, a pellet, a capsule, a tablet (including a single-layered tablet, a double-layered tablet, and a pressed core tablet), dry syrups or granules. However, embodiments are not limited thereto. For example, the oral solid formulation may be in the form of a capsule, a single-layered tablet, or a double-layered tablet. When the oral solid formulation is in the form of a capsule, the capsule may include granules, tablets, or the like therein.

The oral solid formulation may further include at least one pharmaceutically acceptable additive, in addition to the active ingredient and the acidifying agent. For example, the pharmaceutically acceptable additive may include at least one material selected from the group consisting of a diluent, a binder, a disintegrant, a lubricant, and any combinations thereof.

The diluent, which may be used to increase quantity, may be selected from the group consisting of mannitol, lactose, starch, microcrystalline cellulose, Ludipress® calcium dihydrogen phosphate, and any combinations thereof. However, embodiments are not limited thereto. The amount of the diluents may be about 1 to about 99 wt %, and in some embodiments, about 20 to about 80 wt %, based on a total weight of the oral solid formulation.

The binder may be selected from the group consisting of povidone, hydroxypropyl cellulose, hydroxypropyl methyl cellulose, polyvinyl alcohol, sodium carboxymethyl cellulose, and any combinations thereof. However, embodiments are not limited thereto. The amount of the binder may be about 0.5 to about 15 wt %, and in some embodiments, about 1 to about 10 wt %, based on a total weight of the oral solid formulation.

The disintegrant may be selected from the group consisting of croscarmellose sodium, crospovidone, sodium starch glycolate, and any combinations thereof. However, embodiments are not limited thereto. The amount of the disintegrant may be about 1 to about 30 wt %, and in some embodiments, about 2 to about 7 wt %, based on a total weight of the oral solid formulation.

The lubricant may be selected from the group consisting of stearic acid, metal salts of stearic acid (for example, calcium stearate, magnesium stearate, and the like), talc, colloid silica, sucrose fatty acid ester, hydrogenated vegetable oil, wax, glyceryl fatty acid esters, glycerol dibehenate, and any combinations thereof. However, embodiments are not limited thereto. The amount of the lubricant may be about 0.3 to about 7 wt %, and in some embodiments, about 0.5 to about 5 wt %, based on a total weight of the oral solid formulation.

In some embodiments, the oral solid formulation may include about 0.1 to about 500 mg of irinotecan or a pharmaceutically acceptable salt thereof as a free base, as an active ingredient in a unit dosage form. The amount of the irinotecan or pharmaceutically acceptable salt thereof as an active ingredient may be about 0.5 to about 50 wt %, and in some embodiments, about 1 to about 40 wt %, based on a total weight of the oral solid formulation.

The oral solid formulation may be administered to mammals, including humans, with any indication of irinotecan or a pharmaceutically acceptable salt thereof. Accordingly, the oral solid formulation may be used for the treatment of cancer, i.e., various types of cancers, including, but not limited to, lung cancer, stomach cancer, pancreatic cancer, non-Hodgkin's lymphoma, uterine cervix cancer, head and neck cancer, brain tumor, and ovarian cancer. In some embodiments, the oral solid formulation may be used for the treatment of colon cancer, for example, colorectal cancer.

The oral solid formulation according to any of the above-described embodiments may be prepared using any method known in the art of preparing an oral solid formulation, for example, in the form of granules, a pellet, a capsule, or a tablet. In some embodiments, the oral solid formulation according to any of the above-described embodiments may be prepared using a method of preparing wet granules or dry granules or an oral solid formulation using wet or dry granules. In some embodiments, the granules may be prepared by wet granulation.

According to another aspect of the present disclosure, a method of preparing an oral solid formulation according to any one of the above-described embodiments includes:

forming granules including irinotecan or a pharmaceutically acceptable salt thereof, a diluent, and a binder;

mixing the granules with a disintegrant and a lubricant to obtain a mixture; and optionally, formulating the resultant mixture, wherein, in the step of forming granules and/or in the step of mixing the granules, an acidifying agent is added.

The above descriptions of the oral solid formulations according to the above-described embodiments may apply to the method of preparing an oral solid formulation according to any of the above-described embodiments.

The forming of granules may be performed using any granulation method known in the art, for example, using wet granulation or dry granulation. In some embodiments, the forming of granules may be performed using wet granulation.

The wet granulation may include mixing a mixture of irinotecan or a pharmaceutically acceptable salt thereof, and a diluent with a binding solution, forming granules, and drying the granules. The acidifying agent may be added to and mixed with at least one of the mixture and the binding solution.

A solvent for the binding solution may be water, ethanol, isopropanol, acetone, or any combinations thereof. The binding solution may be prepared by adding a binder and any additive available in the pharmaceutical field, for example, a surfactant, a buffer, or a combination thereof, to a solvent. For example, the binding solution may be prepared by dissolving a hydrophilic binder in ethanol.

The drying may be performed at a temperature not exceeding about 60° C., and in some embodiments, a temperature not exceeding about 50° C., and in some other embodiments, not exceeding about 40° C., and in still other embodiments, at a temperature of about 20° C. to about 40° C., by taking into account the stability of the active ingredient, by air drying, fluid bed drying, or oven drying.

The dry granulation may include granulating a mixture including irinotecan or a pharmaceutically acceptable salt thereof, a diluent, a disintegrant, and a binder by roller compaction or direct compression. For example, the dry granulation may be performed by roller compaction. Roller compaction is a granulation method where powder is compacted with a constant pressure while the powder is fed into the gap between two rollers. The roller compaction may be performed using a roller compactor. The roller-compacted mixture may be further subjected to grinding and sieving processes with a grinder (e.g., a fitz mill), an oscillator, or the like, if necessary.

In the dry granulation, the acidifying agent may be added to the mixture comprising irinotecan or a pharmaceutically acceptable salt thereof, a diluent, a disintegrant, and a binder.

In the mixing of the granules with a disintegrant and a lubricant, the disintegrant may be any disintegrants available for granule-containing capsule preparation. In some embodiments, the disintegrant may be selected from the group consisting of croscarmellose sodium, crospovidone, sodium starch glycolate, low-substituted hydroxypropyl cellulose, and any combinations thereof. For example, the disintegrant may be croscarmellose sodium. The lubricant may be selected from the group consisting of magnesium stearate, talc, sodium stearyl fumarate, and any combinations thereof. For example, the lubricant may be a combination of talc and sodium stearyl fumarate. In the mixing of the granules with a disintegrant and a lubricant, the acidifying agent may also be added.

The formulating may be performed using any known method in the art of preparing a solid formulation using granules, for example, using any known method of formulating tablets, capsules, or dry syrups.

MODE OF THE INVENTION

One or more embodiments of the present disclosure will now be described in detail with reference to the following examples. However, these examples are only for illustrative purposes and are not intended to limit the scope of the one or more embodiments of the present disclosure.

Examples 1 to 3: Preparation of Tablets Including Acidifying Agent (1)

Irinotecan hydrochloride trihydrate (Dongwoo Fine-Chem, Korea), lactose, and microcrystalline cellulose were mixed together (pre-mixing) according to the compositions of Table 1, followed by adding a binding solution which was acidified by adding and dissolving citric acid, lactic acid, or acetic acid added as an acidifying agent in a binding solution of povidone dissolved in a mixture of ethanol and water (7:3) to the mixture, granulating, drying, and sieving with a 20-mesh sieve, to thereby prepare irinotecan wet granules.

Croscarmellose sodium was then added to the obtained irinotecan wet granules and mixed (mixing) together, followed by adding magnesium stearate to the mixture, mixing the mixture together (final mixing), and tableting the final mixture with a rotary tablet press (GRC-18, available from Sejong Pharmatech Co., Ltd., Korea) to form tablets having a hardness of about 5 to about 12 kp.

TABLE 1

| | | Amount (mg) | | |
|---|---|---|---|---|
| Ingredient | | Example 1 | Example 2 | Example 3 |
| Pre-mixing | Irinotecan hydrochloride trihydrate | 21.73 | 21.73 | 21.73 |
| | Lactose | 42.00 | 42.00 | 42.00 |
| | Microcrystalline cellulose | 99.20 | 111.20 | 114.20 |
| Binding solution | Povidone | 6.00 | 6.00 | 6.00 |
| | Citric acid | 20.00 | — | — |
| | Lactic acid | — | 8.00 | — |
| | Acetic acid | — | — | 5.00 |
| | Ethanol/water | (40.00) | (40.00) | (40.00) |
| Mixing | Croscarmellose sodium | 10.00 | 10.00 | 10.00 |
| Final mixing | Magnesium stearate | 2.00 | 2.00 | 2.00 |
| | Total weight | 200.93 | 200.93 | 200.93 |

EXAMPLES 4 to 6: Preparing Tablets Including Different Amounts of Acidifying Agent Tablets of Examples 4 to 6 were prepared in the same manner as in Example 1, according to the compositions of Table 2, except that different amounts of citric acid were used as an acidifying agent.

TABLE 2

| | | Amount (mg) | | |
|---|---|---|---|---|
| Ingredient | | Example 4 | Example 5 | Example 6 |
| Pre-mixing | Irinotecan hydrochloride trihydrate | 21.73 | 21.73 | 21.73 |
| | Lactose | 42.00 | 42.00 | 42.00 |
| | Microcrystalline cellulose | 104.20 | 109.20 | 114.20 |
| Binding solution | Povidone | 6.00 | 6.00 | 6.00 |
| | Citric acid | 15.00 | 10.00 | 5.00 |
| | Ethanol/water | (40.00) | (40.00) | (40.00) |
| Mixing | Croscarmellose sodium | 10.00 | 10.00 | 10.00 |
| Final mixing | Magnesium stearate | 2.00 | 2.00 | 2.00 |
| | Total weight | 200.93 | 200.93 | 200.93 |

Comparative Examples 1 to 3: Preparation of Tablets Including Basifying Agent

Tablets of Comparative Examples 1 to 3 were prepared according to the compositions of Table 3 in the same manner as in Example 1 except that no acidifying agent was used (Comparative Example 1), and calcium carbonate (Comparative Example 2) or meglumin (Comparative Example 3) as a basifying agent was used instead of the acidifying agent.

TABLE 3

| | | Amount (mg) | | |
|---|---|---|---|---|
| Ingredient | | Comparative Example 1 | Comparative Example 2 | Comparative Example 3 |
| Pre-mixing | Irinotecan hydrochloride trihydrate | 21.73 | 21.73 | 21.73 |
| | Lactose | 42.00 | 42.00 | 42.00 |
| | Microcrystalline cellulose | 119.20 | 114.2 | 114.2 |
| Binding solution | Povidone | 6.00 | 6.00 | 6.00 |
| | Citric acid | — | — | — |
| | Calcium carbonate | — | 5.00 | — |
| | Meglumin | — | — | 5.00 |
| | Ethanol/water | (40.00) | (40.00) | (40.00) |
| Mixing | Croscarmellose sodium | 10.00 | 10.00 | 10.00 |
| Final mixing | Magnesium stearate | 2.00 | 2.00 | 2.00 |
| | Total weight | 200.93 | 200.93 | 200.93 |

Test Example 1: Comparative Evaluation of pH

The tablets of Examples 1 to 6 and Comparative Examples 1, 2, and 3 were subjected to a dissolution test according to the paddle method in the USP with 900 mL of purified water. The pH of each dissolution medium after 30 minutes of the dissolution test was measured. The results are shown in Table 4.

TABLE 4

|    | Example 1 | Example 2 | Example 3 | Example 4 | Example 5 | Example 6 | Comparative Example 1 | Comparative Example 2 | Comparative Example 3 |
|----|-----------|-----------|-----------|-----------|-----------|-----------|-----------------------|-----------------------|-----------------------|
| pH | 3.9 | 4.0 | 4.0 | 4.2 | 4.4 | 4.7 | 7.0 | 9.4 | 9.6 |

Referring to Table 4, the dissolution media from the tablets of Examples 1 to 6 prepared using an acidifying agent after 30 minutes of the dissolution test were found to have a pH lower than 5.0, while the media from the tablets of Comparative Examples 1, 2, and 3 prepared using no acidifying agent or using a basifying agent were found to have a pH greater than 5.0.

Test Example 2: Dissolution Test

The tablets of Examples 1 to 6 and Comparative Examples 1, 2, and 3 were subjected to a dissolution test according to the paddle method in the USP with 900 mL of purified water. Test samples were taken after 30 minutes of the dissolution test, and analyzed by liquid chromatography under the following conditions to calculate the dissolution rate of irinotecan hydrochloride in each of the samples. The results are shown in Table 5 and FIG. 1.

Column: Stainless steel column (lnertsil ODS-2, having an inner diameter of about 4.6 mm and a length of about 150 mm) packed with C18 (having a particle diameter of about 5 μm) for liquid chromatography Column Temperature: 30° C.

Injection volume of sample: 20 μL

Mobile phase: a mixed solution of methanol including 0.005 mol/L of sodium 1-heptanesulfonate and acetic acid-sodium acetate buffer (pH 4.0), in the volume ratio of 11:9

Flow rate: 1.0 mL/min

Detector: UV-absorption detector (measurement wavelength: 254 nm)

TABLE 5

|        | Example 1 | Example 2 | Example 3 | Example 4 | Example 5 | Example 6 | Comparative Example 1 | Comparative Example 2 | Comparative Example 3 |
|--------|-----------|-----------|-----------|-----------|-----------|-----------|-----------------------|-----------------------|-----------------------|
| 30 min | 89.9 | 93.3 | 90.8 | 85.4 | 82.8 | 80.1 | 68.2 | 49.1 | 47.8 |

As shown in Table 5 and FIG. 1, the tablets of Examples 1, 2, 3, 4, 5, and 6 prepared using an acidifying agent were found to have a high dissolution rate of about 80% or greater in 30 minutes. The higher the amount of the acidifying agent, the higher the dissolution rate of the active ingredient in 30 minutes. However, the tablets of Comparative Examples 1, 2, and 3 using no acidifying agent or a basifying agent were found to have a dissolution rate of about 80% or less in 30 minutes, which is lower than the dissolution rates of the tablets of Examples 1, 2, 3, 4, 5, and 6.

Test Example 3: Analysis of Related Compound

To evaluate storage stability of the tablets prepared in Examples 1, 2, 3, 4, 5, and 6 and Comparative Examples 1, 2, and 3, the amounts of unknown related compounds and a total related compound were measured under the analysis conditions of Table 6. In particular, to evaluate storage stability of with time, the tablets were put into high-density polyethylene (HDPE) bottles and stored in a 60° C. chamber for 2 weeks or 4 weeks, followed by measuring the amounts of related compounds produced after 2 weeks or 4 weeks. The analysis results are shown in Tables 7 and 9 and FIGS. 2 and 3.

TABLE 6

| Detector | UV-absorption detector (measurement wavelength: 220 nm) |
|---|---|
| Column | Stainless steel column (having an inner diameter of about 4.6 mm and a length of about 250 mm) packed with C18 (having a particle diameter of about 5 μm) |
| Column temperature | 25° C. |
| Mobile phase | Solution A - A solution obtained by dissolving 2.72 g monobasic potassium phosphate in 900 mL of purified water, pH-adjustment with phosphoric acid to pH 3.5 ± 0.05, and adding purified water to a volume of 1 L.<br>Solution B - Acetonitrile:Methanol = 3:2 (v/v) |

|  | Time (min) | Mobile phase A (%) | Mobile phase B (%) |
|---|---|---|---|
| Gradient program | 0 | 80 | 20 |
|  | 40 | 30 | 70 |
|  | 45 | 30 | 70 |
|  | 50 | 80 | 20 |
|  | 60 | 80 | 20 |

| Flow rate | 1.0 mL/min |
|---|---|
| Injection volume | 10 μl |
| Analysis time | 60 min |

TABLE 7

| | Unknown related compound | | | | | | | | |
|---|---|---|---|---|---|---|---|---|---|
| | Example | | | | | | Comparative Example | | |
| | 1 | 2 | 3 | 4 | 5 | 6 | 1 | 2 | 3 |
| 0 week | 0.10 | 0.09 | 0.10 | 0.11 | 0.10 | 0.12 | 0.09 | 0.10 | 0.11 |
| 2 weeks | 0.07 | 0.09 | 0.09 | 0.11 | 0.12 | 0.15 | 0.14 | 0.15 | 0.17 |
| 4 weeks | 0.05 | 0.08 | 0.09 | 0.13 | 0.14 | 0.19 | 0.20 | 0.25 | 0.26 |

TABLE 8

| | Total related compound | | | | | | | | |
|---|---|---|---|---|---|---|---|---|---|
| | Example | | | | | | Comparative Example | | |
| | 1 | 2 | 3 | 4 | 5 | 6 | 1 | 2 | 3 |
| 0 week | 0.38 | 0.38 | 0.35 | 0.37 | 0.38 | 0.39 | 0.42 | 0.41 | 0.41 |
| 2 weeks | 0.39 | 0.38 | 0.33 | 0.38 | 0.40 | 0.42 | 0.46 | 0.50 | 0.48 |
| 4 weeks | 0.36 | 0.37 | 0.34 | 0.40 | 0.43 | 0.45 | 0.52 | 0.58 | 0.57 |

As shown in Tables 7 and 8 and FIGS. 2 and 3, the tablets of Examples 1 to 6 prepared using an acidifying agent were found to have nearly no increase in related compounds for 4 weeks, while the tablets of Comparative Examples 1, 2, and 3 prepared using no acidifying agent or using a basifying agent were found to have a remarkable increase in related compounds, compared to Examples 1 to 6.

While this invention has been particularly shown and described with reference to preferred embodiments thereof, it will be understood by those skilled in the art that various changes in form and details may be made therein without departing from the spirit and scope of the invention as defined by the appended claims. The disclosed embodiments should be considered in descriptive sense only and not for purposes of limitation. Therefore, the scope of the invention is defined not by the detailed description of the invention but by the appended claims, and all differences within the scope will be construed as being included in the present invention.

The invention claimed is:

1. An oral solid formulation comprising:
    wet granules comprising
        irinotecan hydrochloride as a sole active ingredient;
        10 wt % to about 23 wt % of lactose and 45 wt % to about 57 wt % of microcrystalline cellulose based on a total weight of the oral solid formulation; and
        an acidifying agent in an amount of 0.2 parts to 5 parts by weight based on 1 part by weight of the irinotecan hydrochloride,
    wherein the acidifying agent is selected from the group consisting of acetic acid, citric acid, lactic acid, and a combination thereof,
    wherein a dissolution rate of the irinotecan hydrochloride of the oral solid formulation is about 80% or greater in initial 30 minutes, when said dissolution rate is measured by a dissolution test using a paddle method of the U.S. Pharmacopoeia (USP) with 900 mL of purified water.

2. The oral solid formulation of claim 1, wherein a mixture of the oral solid formulation and the purified water has a pH of about 1 to 5 in the initial 30 minutes during the dissolution test.

3. The oral solid formulation of claim 1, wherein the oral solid formulation is in the form of a capsule or a tablet.

4. A method of treating a cancer of a subject in need thereof, comprising administering the oral solid formulation of claim 1 to the subject.

5. A method of preparing an oral solid formulation according to claim 1, the method comprising:
    forming granules comprising irinotecan hydrochloride as a sole active ingredient, 10 wt % to about 23 wt % of lactose and 45 wt % to about 57 wt % of microcrystalline cellulose based on a total weight of the oral solid formulation; a diluent, and a binder;
    mixing the granules with a disintegrant and a lubricant to obtain a mixture; and formulating the resultant mixture into the oral solid formulation, wherein, the step of forming granules and/or mixing the granules comprises adding an acidifying agent,
    wherein the step of forming granules is performed by wet granulation, wherein the acidifying agent is selected from the group consisting of acetic acid, citric acid, lactic acid, and a combination thereof; and an amount of the acidifying agent is from about 0.2 parts to about 5 parts by weight based on 1 part by weight of the irinotecan hydrochloride, and
    wherein a dissolution rate of the irinotecan hydrochloride of the oral solid formulation is about 80% or greater in initial 30 minutes, when said dissolution rate is measured by a dissolution test using a paddle method of the U.S. Pharmacopoeia (USP) with 900 mL of purified water.

6. The method of claim 5, wherein the wet granulation comprises forming granules by granulating a mixture of the irinotecan hydrochloride and the diluent in combination with a binding solution including the binder, wherein the acidifying agent is added to the mixture and/or the binding solution.

7. The method of claim 5, wherein, during the dissolution test, a mixture of the oral solid formulation and the purified water has a pH of about 1 to 5 in initial 30 minutes during the dissolution test.

8. The method of claim 5, wherein the oral solid formulation is in the form of a capsule or a tablet.

* * * * *